United States Patent [19]

Parlman

[11] 4,267,394

[45] May 12, 1981

[54] PHENOL ALKYLATION

[75] Inventor: Robert M. Parlman, Bartlesville, Okla.

[73] Assignee: Phillips Petroleum Company, Bartlesville, Okla.

[21] Appl. No.: 23,354

[22] Filed: Mar. 23, 1979

[51] Int. Cl.³ .............................................. C07C 37/11
[52] U.S. Cl. .................................. 568/792; 568/787; 568/804
[58] Field of Search ............... 568/792, 804, 787, 792, 568/781

[56] References Cited

U.S. PATENT DOCUMENTS

| 2,445,735 | 7/1948 | Kitchen | 568/792 |
|---|---|---|---|
| 2,480,254 | 8/1949 | Mavity | 568/787 |
| 2,544,818 | 3/1951 | Axe | 568/792 |
| 2,652,434 | 9/1953 | Johnstone | 568/792 |
| 2,916,524 | 12/1959 | Reese | 568/787 |
| 3,707,569 | 12/1972 | Van Sorge | 568/794 |
| 3,764,630 | 10/1973 | Van Sorge | 568/794 |
| 3,878,255 | 4/1975 | Norell | 568/785 |
| 3,972,836 | 8/1976 | Van Sorge | 568/794 |

FOREIGN PATENT DOCUMENTS

| 1020635 | 12/1957 | Fed. Rep. of Germany | 568/787 |
|---|---|---|---|
| 38-18682 | 9/1963 | Japan | 568/792 |
| 49-28502 | 7/1974 | Japan | 568/792 |
| 481909 | 4/1938 | United Kingdom | 568/792 |
| 497721 | 12/1938 | United Kingdom | 568/792 |
| 172339 | of 1965 | U.S.S.R. | 568/792 |

OTHER PUBLICATIONS

Zargorodnii, "Chemical Abstract", 41, 5477 (1947).
Chemical Abstract, 50 34689.
Olah, "Friedal–Crafts & Related Reactions", II, Part 1, pp. 556 & 589.

*Primary Examiner*—Werren B. Lone

[57] ABSTRACT

A process for selectively alkylating a phenolic compound in the ortho-position which comprises reacting a phenolic compound with an alkanol in the presence of a boron trifluoride etherate catalyst and optionally in the presence of a solvent such as aqueous and non-aqueous inorganic acids.

9 Claims, No Drawings

PHENOL ALKYLATION

BACKGROUND OF THE INVENTION

This invention relates to the alkylation of phenolic compounds. In accordance with another aspect, this invention relates to the alkylation of phenols wherein the principal substitution is in the ortho-ring position. In another aspect, this invention relates to the liquid phase alkylation of phenols with alcohols in the presence of a catalyst selected for the production of ortho-substituted phenolic products. In accordance with a further aspect, this invention relates to the alkylation of phenols using a boron trifluoride etherate catalyst wherein the principal substitution is in the ortho-ring position.

The alkylation of phenols with alcohols, alkyl halides and olefins is old per se. It is further known and recognized that the benzene nucleus in phenolic compounds is very susceptible to alkylation in the presence of conventional alkylation catalysts such as sulfuric acid, aluminum chloride, zinc chloride, hydrogen fluoride and the like. However, this very ease of alkylation often is a disadvantage when the synthesis of specific monoalkylated derivatives of phenols are desired. Further complications involved in phenl alkylation are attributed to the reactivity of the phenolic group toward alkylating agents giving rise to undesirable aralkylethers. Thus, in the alkylation of phenol and cresols with butyl alcohol or butylenes, for example, the art shows yields of mono-alkyl derivatives seldom exceeding 50 mole percent and more often in the neighborhood of 30-40 percent. The balance of the products in such cases are aralkyl ethers and polysubstituted phenols.

The use of boron fluoride or, more precisely, the complex of boron trifluoride and orthophosphoric acid is described in U.S. Pat. No. 2,544,818 as a catalyst for the alkylation of phenol with an olefin such as propylene to give a mixture of ortho- and para-isopropylphenol. No mention is made of the selectivity of the products. However, the reaction which is run in a paraffin solvent requires a water wash followed by an aqueous alkali extraction prior to distillation.

A further reference, "Friedal-Crafts and Related Reactions", by George Olah, Vol. II, Part I, page 566, discloses a process of alkylating phenol with isopropyl alcohol using a boron trifluoride catalyst to give yields of 32% ortho-isopropylphenol, 16% para-isopropylphenol and 13% 2,4-diisopropylphenol isopropyl ether. This is a 52% selectivity of ortho-isopropylphenol.

Several additional references disclose the vapor phase alkylation of phenols with alcohols to give ortho alkylated phenols. All of these references employ other type catalyst and report reaction conditions above 200° C. This cited art is U.S. Pat. Nos. 3,707,569; 3,751,488; 3,764,630; and 3,972,836.

Thus, it would be advantageous if mono orthosubstituted phenols could be prepared in high yields and high selectivity. It would also be of some economic advantage if the desired product could be easily separated and purified without employing additional operations such as washings, etc.

An object of this invention is to provide an improved process for the alkylation of phenols with alcohols.

Another object of this invention is to provide a process of producing ortho-alkylated phenols in high yields and high selectivity.

A further object of this invention is to provide a catalyst selective for the production of ortho-alkylated phenols.

Other objects, aspects, and the several advantages of this invention will become apparent to one skilled in the art upon reading the specification and appended claims.

The Invention

According to the invention, there is provided a process for selectively alkylating a phenolic compound in the ortho-position by reacting a phenolic compound with an alkanol in the presence of a born trifluoride etherate catalyst.

More specifically, the present invention comprises a process of liquid phase alkylation of phenolic compounds having at least one ortho-hydrogen by reaction with an alkanol in the presence of a catalytically effective amount of a catalyst consisting essentially of a dialkylether complex of boron trifluoride at reaction conditions sufficient to selectively alkylate the phenolic compound in the ortho-position to the significant reduction of alkylation in the meta- and para-position.

In accordance with a preferred embodiment, the alkylation of phenols with alcohols using a boron trifluoride etherate catalyst is carried out in a solvent of an aqueous inorganic acid which facilitates and enhances product separation.

Reactants

The present invention is broadly applicable to the alkylation of phenolic compounds having at least one orthohydrogen. Phenolic compounds useful in this invention are of the general formula

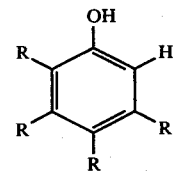

wherein each R is a monovalent substituent such as hydrogen, or an alkyl, aryl or alkylaryl radical containing 1 to 12 carbon atoms, e.g., methyl, ethyl, propyl, phenyl, o-methylphenyl, p-methylphenyl, 2,6-xylyl, and the like. Especially useful starting materials are phenol (R is hydrogen), o-cresol, m-cresol, p-cresol, o-phenylphenol, and 3,5-xylenol. Phenol is a preferred starting material.

Alcohols or alkanols useful in this invention can be represented by the formula

wherein R' is an alkyl or cycloalkyl radical containing 1 to 12 carbon atoms. Illustrative alcohols are those wherein R' is methyl, ethyl, n-propyl, isopropyl, n-butly, t-butyl, hexyl, octyl, 2-ethylhexyl, decyl, dodecyl and cyclohexyl. It is presently preferred to utilize lower alkanols having from 1-6, inclusive, carbon atoms.

The amount of alcohol employed should be in a slight molar excess to the amount of phenol used. Generally, a molar ratio of alcohol to phenol will be about 1.1 to 1.

Catalyst

The catalysts useful in this invention are dialkylether complexes of boron trifluoride and are represented by the formula $$BF_3 \cdot OR_2''$$

wherein R" is an alkyl radical containing 1–3 carbon atoms. The preferred catalyst is boron trifluoride complexed with diethyl ether. The amount of catalyst used can vary appreciably, but the amounts used will be a catalytically effective amount sufficient to cause selective alkylation of the phenolic compound in the ortho-position. In the current invention, five milliliters (5.77 grams, 0.041 moles) of boron trifluoride diethyl etherate per mole of phenol was used. However, in general, the amounts of catalysts per mole of phenol will vary from 0.01 moles to 0.10 moles.

Solvents

The solvents useful in this invention include aqueous and non-aqueous inorganic acids such as HCl, $H_2SO_4$, $H_3PO_4$, $HNO_3$ and the like. The preferred acid solvent is $H_3PO_4$. The ortho-alkylated phenolic products of this invention are insoluble in inorganic acids at room temperature (two phase) which facilitates and enhances product separation.

Reaction Conditions

The pressure employed in carrying out the reaction can vary appreciably, but generally will be sufficient to maintain liquid phase conditions, thus, atmospheric as well as elevated pressure can be used. Temperature, however, will range between ambient room temperature and about 120° C., preferably between about 70°–90° C. Above about 120° C., isomerization can occur from the ortho-position to the meta-position.

Product Separation

The products of the invention can be separated and recovered by conventional methods such as distillation, crystallization, derivatives from subsequent reactions, etc. Frequently, ortho- and meta- and sometimes para-substituted isomers of phenolic compounds cannot be separated for analysis by Gas Liquid Chromatography (GLC) when present as mixtures. For this reason, the current invention employs a method of analysis whereby the hydroxyl group of the phenol is converted to a trimethylsiloxy group and then analyzed by GLC. The ortho- and meta-isomers are easily separated.

The following examples serve to illustrate the operability of this invention.

EXAMPLE I

This example is considered a control and illustrates the alkylation of phenol with isopropanol using $H_3PO_4$ as a catalyst and solvent. To a 250 milliliter round bottom flask supplied with a mechanical stirrer, thermometer, condenser and heating mantle was added 100 milliliters of concentrated (85%) $H_3PO_4$, 47 grams (0.5 moles) phenol and 33 grams (0.55 moles) isopropyl alcohol. The mixture was stirred vigorously while being heated to 120° C. After about 9 hours, the reaction was cooled. The top organic layer was removed and 0.3 milliliters was treated with 1 milliliter of Regisil® silylating agent (N,O-bis[trimethylsilyl]-trifluoroacetamide from Regis Chemical Co.). This reagent reacts with the hydroxy group of the phenol forming a trimethylsiloxy group. The amount of ortho-, meta-, and para-substituted derivatives are then easily measured by GLC analysis conducted on a 10 ft. × ⅛ in. column containing Carbowax 20M at 180° C. isothermally with a 30 milliliter/min. helium flow. The reaction was repeated at various temperatures and solvent concentrations. These results are listed in Table I. They indicate the level of $H_3PO_4$ solvent should be greater than 25 milliliters solvent per 0.5 moles of phenol (compare Runs 1 and 2) to give a higher phenol conversion and better separation. Above 25 milliliters of solvent the reactants and products form one top layer and the acid solvent forms a heavier bottom layer. This allows easier separation between product and solvent. When the temperature exceeds about 120° C. (Runs 3 and 4), the selectivity of the ortho-substituted phenol is reduced, probably because of isomerization, and by-product ethers are formed.

TABLE I

Effects of Temperature and Solvent Concentration
Alkylation of Phenol with Isopropyl Alcohol

| Run No. | Conc. $H_3PO_4$, ml | Reaction Conditions Temp., °C. | Time, Hrs. | Phenol | Wt. % Yield by GLC o-Isopropyl Phenol | p-Isopropyl Phenol | Isopropyl Phenyl Ether | % Selectivity, o-Isopropyl Phenol |
|---|---|---|---|---|---|---|---|---|
| 1 | 25 | 115 | 6 | 62 | 7 | 3 | — | 70 |
| 2 | 50 | 115 | 6 | 21 | 24 | 11 | — | 68 |
| 3 | 100 | 140 | 12 | 29 | 35 | 23 | 7 | 53 |
| 4 | 150 | 140 | 12 | 21 | 33 | 19 | 14 | 50 |
| 5 | 100 | 120 | 9 | 40 | 36 | 15 | — | 70 |

EXAMPLE II

This example is another control and illustrates the use of adding $BF_3$ to the reaction mixture as a catalyst. A $BF_3$ catalyst was employed for the alkylation of phenol with isopropyl alcohol as previously reported by George Olah. In this reaction, the temperature was between 115° C. to 160° C. with a 52% selectivity to the ortho-derivative. The reaction described in Example I was repeated except a 1:1 wt. ratio of $H_3PO_4$ to $BF_3$ was employed as solvent and catalyst. The reaction temperature was 130° C. to provide more of the ortho-derivative since the Olah reference reported a 1:2 wt. ratio of para to ortho as low as 115° C. The results shown in Table II indicate an even lower selectivity to the ortho derivative. Although the amount of phenol remaining after the heating period indicates a high conversion, there is not much ortho derivative present while the amounts of heavies is greatly increased.

TABLE II

Effect of BF$_3$ on Product Distribution and Yields

| Run No. | H$_3$PO$_4$ . BF$_3$ Complex, ml | Reaction Conditions Temp. °C. | Time, Hrs. | Phenol | Wt. % Yield by GLC o-Isopropyl Phenol | p-Isopropyl Phenol | Isopropyl Phenyl Ether | Unknowns | % Selectivity o-Isopropyl Phenol |
|---|---|---|---|---|---|---|---|---|---|
| 1 | 50 | 130 | 8 | 18 | 24 | 27 | 15 | 16 | 29 |
| 2 | 100 | 130 | 8 | 12 | 10 | 44 | 19 | 15 | 11 |
| 3 | 100 | 130 | 4 | 15 | 13 | 63 | — | 8 | 15 |

EXAMPLE III

This example is another control and illustrates the use of an alternate alkylation catalyst, zinc chloride/hydrochloric acid complex. The reaction described in Example I was repeated except the H$_3$PO$_4$ solvent was replaced with concentrated hydrochloric acid and zinc chloride was added. The results, listed in Table III, show good ortho-isopropylphenol selectivity but low phenol conversion.

TABLE III

Effects of HCl . ZnCl$_2$ Catalyst on Alkylation of Phenol

| Run No. | Solvent . Catalyst HCl | ZnCl$_2$ | Reaction Conditions Temp. °C. | Time, hrs. | Phenol | Wt. % Yield by GLC o-Isopropyl Phenol | p-Isopropyl Phenol | % Selectivity o-Isopropyl Phenol |
|---|---|---|---|---|---|---|---|---|
| 1 | 100 ml | 25g | 90–110 | 6 | 82 | 9 | 3.7 | 70 |
| 2 | 100 ml | 50g | 90–110 | 6 | 80 | 12 | 5 | 70 |

EXAMPLE IV

This example illustrates the invention by using a BF$_3$.etherate catalyst. the reaction described in Example I was repeated except 25 milliliters of BF$_3$.etherate was added to the 100 milliliters of H$_3$PO$_4$ solvent. The results, listed in Table IV, show high selectivity to the ortho derivative. In addition, after 10 hrs. heating, a high (68%) yield of ortho-isopropylphenol, is produced with only a small yield (9%) of the para derivative. The low yield of ortho-isopropylphenol after only 4 to 6 hrs. heating (Runs 1 and 2) coupled with the low amount of phenol present (25–34 wt. %) leaves a significant amount of reactant or product unaccounted for. This unaccounted material was not analyzed for but was thought to be isopropyl phenyl ether, an intermediate that rearranges during continued heating from the ether to the ortho- and para-alkylated derivatives.

TABLE IV

Effects of BFl$_3$ . Etherate Catalyst on the Alkylation of Phenol

| Run No. | Solvent + Catalyst H$_3$PO$_4$ | BF$_3$ | Reaction Conditions Temp. °C. | Time, hrs. | Phenol | Wt. % Yield by GLC o-Isopropyl Phenol | p-Isopropyl Phenol | % Selectivity o-Isopropyl Phenol |
|---|---|---|---|---|---|---|---|---|
| 1 | 100 ml | 25 ml | 110 | 4 | 34 | 32 | 5 | 86 |
|   |        |       |     | 6 | 25 | 38 | 6 | 86 |
|   |        |       |     | 10 | 23 | 68 | 9 | 88 |

The preceding data is summarized in Table V which shows the highest yield and selectivity of the mono-substituted ortho-alkylated phenol occurs when a BF$_3$.etherate catalyst is employed as compared to three other catalyst systems tested.

TABLE V

Summary

| Example | Solvent | Catalyst | Phenol | Wt. % by GLC o-Isopropyl Phenol | p-Isopropyl Phenol | % Selectivity, o-Isopropyl Phenol |
|---|---|---|---|---|---|---|
| I | H$_3$PO$_4$ | H$_3$PO$_4$ | 40 | 36 | 15 | 70 |
| II | H$_3$PO$_4$ | BF$_3$ | 15 | 13 | 63 | 15 |
| III | HCl | ZnCl$_2$ | 80 | 12 | 5 | 70 |
| IV (Invention) | H$_3$PO$_4$ | BF$_3$ . Etherate | 23 | 68 | 9 | 88 |

I claim:

1. A process for the production of mono-substituted ortho-alkylated phenolic compounds in high yields and selectivity which comprises reacting
   (a) at least one monohydroxy, monocyclic phenolic compound having at least one ortho-hydrogen represented by the general formula

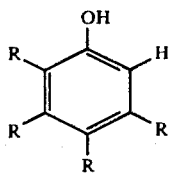

wherein each R is a monovalent substituent such as hydrogen, or an alkyl, aryl or alkylaryl radical containing 1 to 12 carbon atoms with (b) a slight molar excess of a monohydroxy alcohol represented by the formula

wherein R' is an alkyl or cycloalkyl radical containing 1 to 12 carbon atoms to the amount of phenolic compound (a) used in the presence of (c) a catalytic amount of a catalyst consisting essentially of a dialkylether complex of boron trifluoride represented by the formula

wherein R" is an alkyl radical containing 1-3 carbon atoms at reaction conditions sufficient to selectively alkylate (a) in the ortho-position to the significant reduction of alkylation in the meta- and para-positions and produce mono-substituted ortho-alkylated phenolic compounds in high yields and high selectivity.

2. A process according to claim 1 wherein said reacting is carried out in (d) an aqueous or non-aqueous inorganic acid in an amount sufficient to facilitate product separation.

3. A process according to claim 1 wherein the pressure is sufficient to maintain liquid phase conditions, the temperature ranges from ambient room temperature to about 120° C. and the amount of (c) present ranges from 0.01 moles to 0.10 moles per mole of (a).

4. A process according to claim 1 wherein (b) is a lower alkanol of up to and including 6 carbon atoms.

5. A process according to claim 4 wherein (b) is isopropanol.

6. A process according to claim 1 wherein
(a) is phenol;
(b) is isopropanol;
(c) is boron trifluoride dialkyl etherate, and the reaction is carried out in
(d) an inorganic acid diluent.

7. A process according to claim 1 wherein phenol is reacted with isopropanol in the presence of a diethyl ether complex of boron trifluoride in phosphoric acid diluent at a temperature of between about 70°-90° C. to produce ortho-isopropyl phenol.

8. A process according to claim 1 wherein the reaction is carried out
(d) in an aqueous or non-aqueous inorganic acid diluent.

9. A process according to claim 8 wherein the diluent is phosphoric acid.

* * * * *